United States Patent [19]

Udovich et al.

[11] 4,339,595

[45] Jul. 13, 1982

[54] HEXA(META-,PARA-CARBOXYPHENYL)-BENZENE COMPOUNDS

[75] Inventors: Carl A. Udovich, Joliet; Ellis K. Fields, River Forest, both of Ill.

[73] Assignee: Standard Oil Company (Indiana), Chicago, Ill.

[21] Appl. No.: 163,529

[22] Filed: Jun. 27, 1980

[51] Int. Cl.$^3$ .................. C07C 69/76; C07C 63/48; C07C 69/773; C07C 51/353; C07C 67/343; C07C 103/82

[52] U.S. Cl. .................. 560/76; 252/51.5 R; 252/57; 260/544 D; 260/544 P; 560/86; 560/88; 560/89; 560/91; 560/96; 562/488; 564/153; 564/157

[58] Field of Search .............. 562/488, 442; 560/76, 560/86, 96, 88, 89, 91; 260/544 D, 544 P; 564/153, 157

[56] References Cited

U.S. PATENT DOCUMENTS 3,954,840  5/1976  Yamashita et al. .................. 562/488
4,131,748  12/1978  Arnold et al. ........................ 562/488

Primary Examiner—Natalie Trousof
Assistant Examiner—Vera C. Clarke
Attorney, Agent, or Firm—William C. Clarke; William T. McClain; William H. Magidson

[57] ABSTRACT

Hexa(meta-,para-carboxyphenyl)benzene compounds. The esters are useful as plasticizers for polyvinylchloride, heat transfer agents, hydraulic fluids, and insulating oils. The acid is suitable as a cross-linking agent for polymers containing hydroxyl or amine groups.

10 Claims, No Drawings

HEXA(META-,PARA-CARBOXYPHENYL)BENZENE COMPOUNDS

BACKGROUND OF THE INVENTION

The field of this invention relates to aromatic polyacyl compounds of polyphenyl structure suitable for use as a cross-linking agent for polymers containing hydroxyl or amine groups. The esters are useful as plasticizers for polyvinylchloride, heat transfer agents, hydraulic fluids, and insulating oils.

A new compound, hexa(meta-, para-carboethoxyphenyl)benzene has been prepared by the cyclotrimerization of 3,3' or 4,4'-dicarboethoxytolan, using dichlorobisbenzonitrilepalladium (II) as a catalyst. As is well known, cobalt octacarbonyl, bis(dibenzylideneacetone) palladium (0) and tri-isobutylaluminumtitanium tetrachloride have been effective for trimerization of hindered acetylenes. However, these catalysts were ineffective in this synthesis.

The preparation of benzene and substituted benzenes such as hexa-substituted benzenes from acetylenic compounds in the presence of specific solvents and catalysts is known in the art. For example, U.S. Pat. No. 2,723,299 teaches the preparation of benzene and styrene from acetylene and vinylacetylene in the presence of a solvent which can be benzene, acetonitrile or tetrahydrofuran and a catalyst such as triphenylphosphine nickel-dicarbonyl or with a co-catalyst compound of copper or mercury halogenide with trialkyl or triarylphosphine, or with a compound of a copper halide with ammonium salts, or with amine-hydrogen halogenide salts. U.S. Pat. No. 2,819,325 teaches the preparation of benzene and alkyl benzenes from 1-alkynes using a chromium oxide containing catalyst with a catalyst support comprising at least one member selected from the group consisting of silica, alumina, zirconia, titania and siliceous natural clays. Belgian Pat. No. 567,744 (CA53:16082d) teaches preparation of substituted benzene compounds by cyclization of mono- or di-substituted acetylene derivatives in the presence of metal carbonyls. Hexaphenylbenzene was prepared from tolan in presence of $Fe(CO)_4$. Phenylacetylene gave 1,2,3,5-tetraphenylbenzene. Hubel et al., *Chem. Ber.* 93, 103-15 (1960) (CA54:9841b) teach that mono- and di-substituted acetylenes heated in the presence of small amounts of metal carbonyl derivatives, with or without solvent, are converted to benzene derivatives. Phenylacetylene with $[Co(CO)_4]Hg$ as catalyst gave hexaphenylbenzene. Similar reactions are taught in British Pat. No. 889,993 (CA58:1394h) and German Patent 1,142,867 (CA59:6317h). U.S. Pat. No. 2,980,741 teaches that divalent nickel hydrocarbon compounds are catalysts for polymerization of di-substituted acetylenes. Hexaphenylbenzene is prepared from diphenyl acetylene with a Grignard reagent as catalyst prepared from mesitylmagnesium bromide and nickel bromide. British Pat. No. 890,542 teaches preparation of tri- and hexa-substituted benzenes by trimerization of substituted acetylenes over a three-component catalyst. The three components of the catalyst system are (1) a titanium compound, a Fe(III) halide or a nickel compound; (2) a metal of Group IA, IIA, IIB or IIIA; (3) a halide of an element of Group IIB, IIIA, IVA or VA. Hexaphenylbenzene as well as other substituted benzenes are prepared. U.S. Pat. No. 3,073,873 teaches preparation of tetrasubstituted butadienes and related olefins by reacting a di-substituted acetylene with an organometallic compound. Tetraphenylbutadiene and alpha-ethyl-cis-stilbene are prepared from diphenylacetylene and triethylaluminum. U.S. Pat. No. 3,082,269 teaches preparation of hexa-substituted benzenes such as hexaphenylbenzene by contacting an acetylenic compound such as diphenylacetylene with a catalyst obtained by reacting a transition metal halide such as $TiCl_4$ with an organometallic compound such as $LiAl(C_7H_{15})_4$. U.S. Pat. No. 3,129,243 teaches preparation of substituted benzene compounds such as hexaphenylbenzene from diphenylacetylene in the presence of a catalyst of iron tetracarbonyl. Preparation of other substituted benzene compounds such as hexa(para-chlorophenyl)benzene and 1,2-diphenyl-3,4,5,6 tetracarbomethoxybenzene are also taught.

In the prior art, it has also been known that the catalytic activity of particular catalysts has been remarkably specific. For example, Franzus et al. report, *J.A.C.S.*, 81 (1959) p1514, that by regulating the ratio of triisobutylaluminum with titanium tetrachloride as cyclizing catalyst for acetylenic compounds, diphenyl acetylene can be trimerized to hexaphenylbenzene only between triisobutylaluminum: titanium tetrachloride ratios of 1:1 to 3:1. In other examples, triethylchromium (III) in tetrahydrofuran cyclizes tolan to hexaphenylbenzene, but also it contributes an ethyl group in a mixed condensation with tolan, yielding 1,2,3,4-tetraphenylbenzene in addition to the normal product, hexaphenylbenzene. Similarly, when tolan (diphenyl acetylene) was added to dimesitylnickel in tetrahydrofuran, small amounts of hexaphenylbenzene were obtained. However, when the order of addition was reversed, with mesitylmagnesium bromide being added to the mutually inert pair, nickel (II) bromide and tolan, the yield of hexaphenylbenzene rose steeply, *J.A.C.S.*, 82 (1960) p6256. Similarly, the specificity of catalysts for cyclizing acetylenic compounds has been further documented; carbonyls of iron, cobalt and nickel (*J.A.C.S.*, 83 (1961) p2944); bis-(benzonitrile)-palladium chloride in nonhydroxylic solvents such as benzene, chloroform and acetone (*J.A.C.S.*, 84 (1962) p2330); nickel-carbonyl-phosphine complexes (*J. Org. Chem.*, 27 (1962) p3930); noble metal halides (i.e., bis(benzonitrile) palladium chloride with methylphenylacetylene and dimethylacetylene (*J.A.C.S.*, 92 (1970) p2276); dibenzylideneacetone-palladium (0) and -platinum (0) complexes (*Chem. Communications* (1971) p1604); cyclobutadienepalladium halide complexes (*J. Organometal Chem.*, 26 (1971) 407-415).

The great number of methods for catalyzed cyclization of acetylenic compounds, however, to the best of our knowledge, has not led to the preparation of substituted hexaphenylbenzenes other than hexa(parachlorophenyl)benzene (U.S. Pat. No. 3,129,243). Accordingly, it is an object of this invention to provide a new group of aromatic polycarboxylic acids of hexa-substituted benzenes. Another object of this invention is to provide a process for making these acids. Another object of this invention is to provide a new polycarboxylic acid and ester, specifically hexa(meta-, para-carboxyphenyl)benzene, hexa(meta-, para-carboalkoxyphenyl)benzene, and hexa(meta-, para-carboaryloxyphenol)benzene and derivatives of these compounds. Other and further objects will be apparent from the following description.

The field of this invention accordingly has three aspects. First, it relates to novel compositions of matter that are hexa(meta-, para-carboxyphenyl)benzene compounds, second, to the method of preparing these compounds. Third, it relates to novel highly cross-linked insoluble compositions of these hexa(meta-, para-carboxyphenyl)benzene compounds with di- and polyfunctional compounds such as di- and polyamine and di- and polyhydroxy compounds, and to linear polymers available from the carboxyl compounds. The insoluble cross-linked compositions are useful as catalyst supports. Linear polymers containing the hexa-(meta-, para-carboxyphenyl)benzene moiety can be prepared by blocking all but two active carboxy sites, then preparing acyl chlorides from the acid and reacting the acyl chloride moieties with required mole ratios of amine or hydroxyl compounds.

These novel hexa(meta-, para-carboxyphenyl)benzene compounds (acids, acyl halides, simple esters, e.g., methyl, etc.) accordingly are desirable for use in the preparation of organic semiconductors, charge-transfer complexes, detergent builders, and as cross-linking agents for polymers.

The esters of these acids with monohydric alcohols containing 1 to 24 carbon atoms can be used as plasticizers for polyvinylchloride (PVC).

It has been found in accordance with this invention that hexa(meta-, para-carboxyphenyl)benzene compounds can be prepared by the cyclotrimerization of 3,3'- or 4,4'-dicarboalkoxytolan or 3,3'- or 4',4'-dicarboaryloxytolan using dichlorobisbenzonitrile-palladium (II) as a catalyst. The hexa(meta-, para-carboalkoxyphenyl)benzene or aryloxy compound can be saponified and converted to hexa(meta-, para-carboxyphenyl)benzene by acidification. Acyl halides can be prepared from the acid by replacing the hydroxyl group of the acid with a halogen. Accordingly, this invention relates to a new family of compositions of matter having the following structural formula

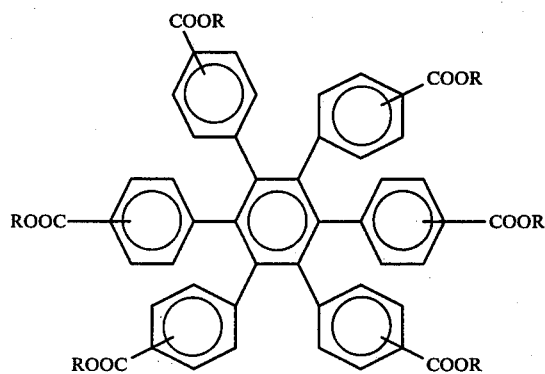

wherein R is selected from the group consisting of hydrogen, alkyl and aryl moieties. When R is hydrogen, the —OR moiety can be replaced with a halogen moiety.

SUMMARY OF THE INVENTION

Hexa(meta-, para-carboxyphenyl)benzene compounds and method for preparation. The esters can be used as plasticizers for polyvinylchloride, heat transfer agents, hydraulic fluids and insulating oils. The acids are cross-linking agents for polymers containing hydroxyl or amino groups.

DETAILS OF THE INVENTION

The compositions of this invention relate to hexa(meta-, para-carboxyphenyl)benzene, and esters and acyl halides thereof such as hexa(meta-, para-carbomethoxyphenyl)benzene, hexa(meta-, para-carboethoxyphenyl)benzene, etc. which are prepared by the cyclotrimerization of 3,3'- or 4,4'-dicarboalkoxytolan or 3,3'- or 4,4'-dicarboaryloxytolan using dichlorobisbenzonitrilepalladium (II) as catalyst. The invention is illustrated by the following equations:

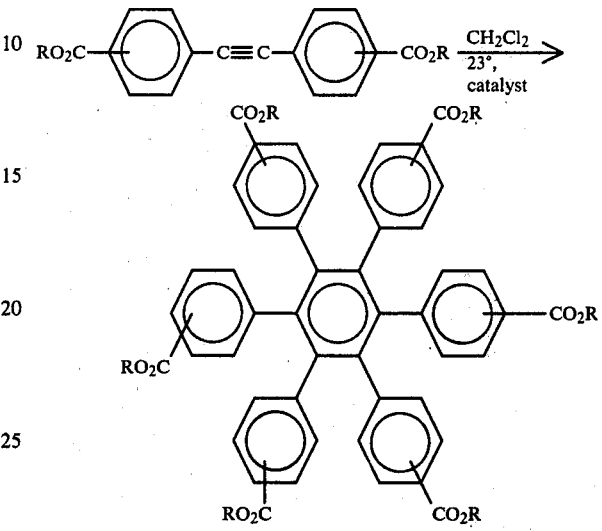

R is an alkyl or aryl group. Dichloromethane is the solvent of choice, although other halogenated hydrocarbons should work equally as well. The catalyst which causes cyclotrimerization is dichlorobisbenzonitrilepalladium (II). The reaction is run at 0°–100° C., 20°–30° C. being preferred.

Hexa(m-, p-carboxyphenyl)benzene may be converted into the corresponding tris-methylenedioxy derivative and the tris-carbonic anhydride with phosgene, and find utility in the preparation of organic semiconductors, charge-transfer complexes and as a builder for surfactants and detergents. Due to its polycarboxylic character, it functions as a cross-linking agent for polymers containing hydroxyl or amino groups. Insoluble compounds useful as catalyst supports can be prepared by reacting the compounds of the instant invention with compounds containing hydroxyl or amino groups such as ethylene glycol, 1,4-butanediol, glycerol, pentaerythritol, hydroquinone, hydroxy-hydroquinone, ethylene diamine, 1,6-hexanediamine, 1,12-dodecanediamine, para-phenylenediamine, oxybisaniline and methylenebisaniline.

A flow diagram for the production of hexa(m-, p-carboalkoxy (or aryloxy)phenyl)benzene is as follows.

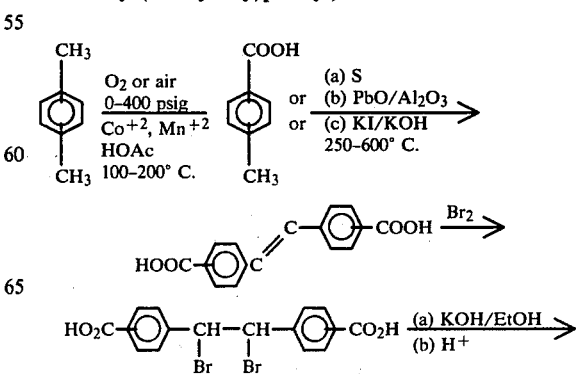

-continued

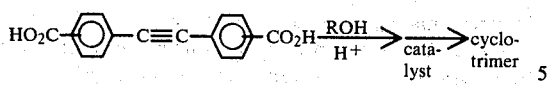

R can be an alkyl or aryl moiety of 1 to 24 carbon atoms. For example, oxidation of p-xylene to p-toluic acid is followed by dehydrodimerization by S, PbO on alumina, or KOH/KI to the 4,4'-stilbenedicarboxylic acid which is converted to the dibromide, dehydrobrominated to the tolan analog, esterified with ROH in the presence of acid, and lastly cyclotrimerized, using dichlorobisbenzonitrilepalladium (II) as a catalyst.

The esters of polyphenyl carboxylic acids of this invention are useful as plasticizers of polyvinylchloride and other polymer formulations. Suitable monohydric alcohols useful for producing the ester include aromatic or aliphatic, straight or branched chain, substituted or unsubstituted compounds of from 1 to 24 carbon atoms. Examples are alcohols such as methyl alcohol, ethyl alcohol, propyl alcohol, butyl alcohol, cyclohexanol, heptyl alcohol, dodecyl alcohol, octyl alcohol, isotridecyl alcohol, stearyl alcohol, oleyl alcohol, tetracosyl alcohol, as well as aromatic hydroxy compounds containing from 6 to 24 carbon atoms such as phenol, naphthol, cresol, parastearylphenol, etc.

Polyphenylbenzene has been taught as an ultraviolet absorber for ultraviolet sensitive polymers wherein by incorporation of a small quantity of a polyphenyl benzene in a polyolefin resin, deterioration from the effects of exposure to ultraviolet light is inhibited over extended periods of time. The compounds of the present invention, because of their molecular structure, have potential as ultraviolet absorbers for ultraviolet sensitive polymers.

The compositions of the present invention have potential of a high degree of compatibility with the polyolefin in which they are incorporated. A convenient method for their incorporation is by addition on a roll mill operated at a temperature in the range between 275° and 400° F.

The resins in which the compositions of our invention are considered to be useful include, broadly, those which are sensitive to ultraviolet light. These include, for example, polyethylene, polypropylene, ethylene-propylene copolymers, poly(vinylchloride), poly(vinyl acetate), vinyl chloride-vinyl acetate copolymers, and poly(vinylidene chloride), as well as polyesters and polyamides. The compositions can be used alone or together with other additives such as fillers, antioxidants, pigments, etc. Mixtures of compositions can be used.

Accordingly, the instant invention relates to a hexa-carboxyphenylbenzene compound of the structural formula

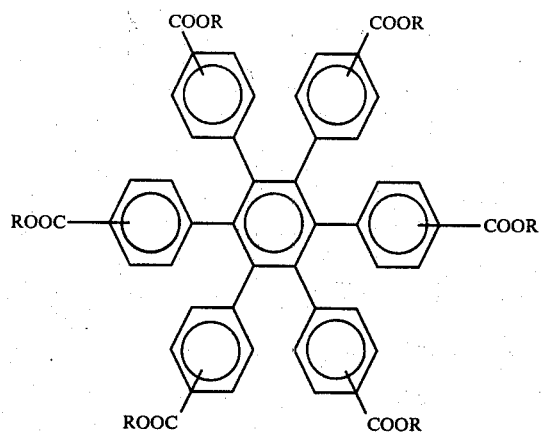

wherein R is selected from the group consisting of hydrogen, alkyl moieties, and aryl moieties. R can be an alkyl group of 1 to 24 carbon atoms or an aryl group of 6 to 24 carbon atoms. When R is hydrogen, the —OR moiety can be replaced with a halogen moiety selected from the group consisting of chlorine, iodine, bromine and fluorine. The instant invention also relates to the reaction product of a hexa-carboxyphenylbenzene compound of the structural formula

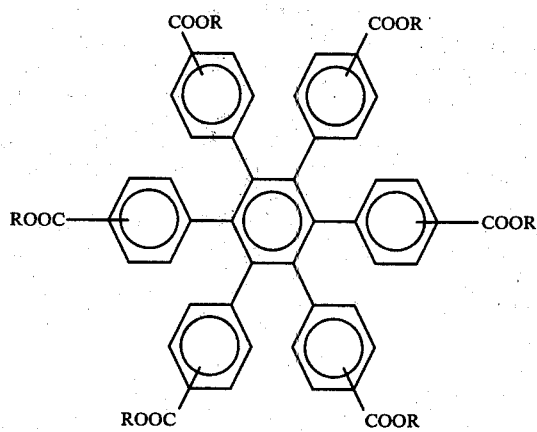

wherein R is hydrogen and a compound selected from the group consisting of ethylene glycol, 1,4-butanediol, glycerol, pentaerythritol, hydroquinone, hydroxyhydroquinone, ethylene diamine, 1,6-hexanediamine, 1,12-dodecanediamine, para-phenylenediamine, oxybisaniline and methylene bisaniline, with the provision that the —OR moiety can be halogen. The instant invention also relates to the process for preparing hexa(meta-, para-carboxyphenyl)benzene compounds of the structural formula

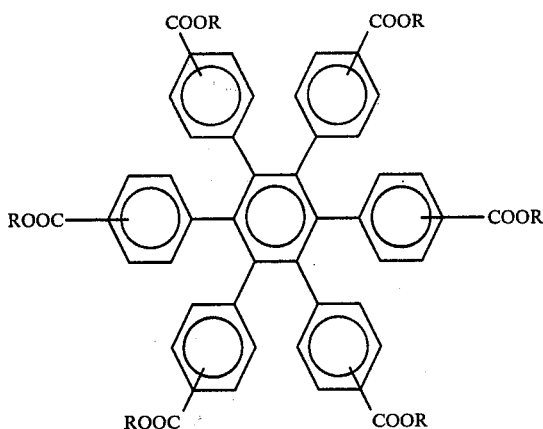

wherein R is selected from the group consisting of hydrogen, alkyl moieties of 1 to 24 carbon atoms and aryl moieties of 6 to 24 carbon atoms which comprises the cyclotrimerization of a compound selected from the group consisting of 3,3'-dicarboalkoxytolan, 4,4'-dicarboalkoxytolan, 3,3'-dicarboaryloxytolan and 4,4'-dicarboaryloxytolan wherein the alkoxy or aryloxy moiety can be from 1 to 24 carbon atoms in the presence of a suitable amount of dichlorobisbenzonitrilepalladium (II) as catalyst.

The following examples serve to illustrate the preparation and application of hexa(meta-, para-carboalkoxyphenyl)benzene and hexa(meta-, para-carboxyphenyl)benzene in accordance with our invention. These examples are to be regarded solely as illustrative and not as restricting the scope of the invention.

EXAMPLE I

In a 250 ml. round-bottom flask equipped with a magnetic stirrer are placed 3.2 g (0.01 m) of 4,4'-dicarboethoxytolan, 1.0 g (0.0026 m) of dichlorobisbenzonitrilepalladium (II), and 75 ml of methylene chloride. The reactor is kept under a positive nitrogen pressure and allowed to stir at 25° C. for 18 hours. The reaction mixture is filtered, affording 0.2 g of a brown palladium-containing precipitate. The solution is treated with 200 ml of hexane to precipitate 3.0 g of a white solid melting at 364° C. The trimer is verified by 13C nmr. The sample gives a spectrum consistent with the structure

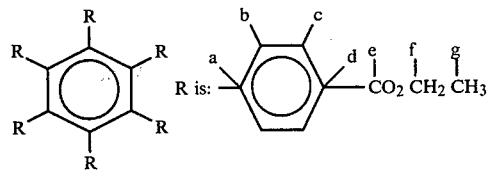

The resonance signal for the central ring carbons occurs at 139.8 ppm. The other chemical shifts are $\delta_a = 144.1$, $\delta_b = 131.0$, $\delta_c = 128.4$, $\delta_d = 128.2$, $\delta_e = 166.3$, $\delta_f = 60.9$ and $\delta_g = 14.2$.

The same procedure may be used to prepare the hexa(m-carboethoxyphenyl)benzene from m-toluic acid.

EXAMPLE II

Ultraviolet absorption spectra were determined for hexa(para-carboxyphenyl)benzene and compared with the spectra of hexaphenylbenzene. Hexa(para-carboxyphenyl)benzene has its most intense absorption at 263 nanometers and begins to absorb appreciably at wavelengths as long as 320 nanometers, whereas hexaphenylbenzene has its most intense absorption at 244 nanometers and does not show appreciable absorption until 275 nanometers. Accordingly, hexa(para-carboxyphenyl)benzene can be an efficient screen for ultraviolet light in polymers. The presence of functional carboxyl groups on hexa(meta-, para-carboxyphenyl)benzene compounds can cause a firm chemical bonding to amino or hydroxyl groups in polyamides or polyesters.

EXAMPLE III

In the procedure of Example I, hexa(p-carboethoxyphenyl)benzene was prepared. The compound was converted to the acid by saponification. A hot solution of 2.5 g of potassium hydroxide in 75 ml ethanol was added to a refluxing solution of 40 g of hexa(p-carboethoxyphenyl)benzene in 20 ml benzene. Heating was continued for 18 hours. The white solid that precipitated was filtered and dried in air. The potassium salt was then dissolved in water. Concentrated hydrochloric acid was added. The acid derivative which formed was collected, washed with water and dried in a vacuum oven at 100° C. Yield was 72%.

Ten g of the acid were placed in a 200 ml flask containing a coated magnetic stirring bar, followed by the introduction of 70 ml $SOCl_2$. Pyridine, 10 ml, was added slowly. Refluxing with stirring continued for 18 hours after which the reaction mixture was cooled to room temperature. The acyl chloride was isolated as a white solid, washed with hexane and dried. After recrystallization from dichloromethane, the yield was approximately 60%. Calculated analysis for $C_{18}H_{24}O_6$: C, 63.39;H,2.67. Found: C,63.49;H,2.73.

Polyamides of 1,6-hexanediamine were prepared from the acyl chloride. Three moles of 1,6-hexanediamine were dissolved in water containing approximately 1 g of $Na_2CO_3$. A solution of 1 mole of the acyl chloride in 400 ml dichloromethane was added to the diamine solution. The resulting polyamide was collected, washed with water and dried in a vacuum oven at 110° C. Yield: 75–80%. The polyamide was insoluble in organic solvents and began to decompose when heated at about 350° C. and did not melt below 400° C.

Polyamides of 1,12-dodecanediamine were prepared in the same manner. This compound demonstrated the same insolubility in organic solvents and also began to decompose at about 350° C. It did not melt below 400° C.

What is claimed is:

1. Hexa-carboxyphenylbenzene compound of the structural formula:

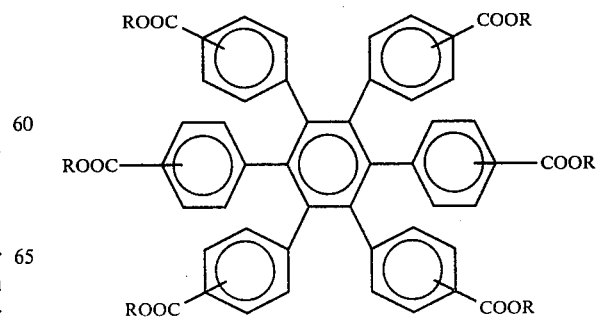

wherein R is selected from the group consisting of hydrogen, alkyl moieties and aryl moieties.

2. The compound of claim 1 wherein R is an alkyl group of 1 to 24 carbon atoms.

3. The compound of claim 1 wherein R is an aryl group of 6 to 24 carbon atoms.

4. The compound of claim 1 wherein said hexa-carboxyphenylbenzene compound is hexa(para-carboxyphenyl)benzene.

5. The compound of claim 1 wherein said hexa-carboxyphenylbenzene is hexa(meta-carboxyphenyl)benzene.

6. The compound of claim 1 wherein R is a methyl moiety.

7. The compound of claim 1 wherein R is an ethyl moiety.

8. A process for preparing hexa(meta-, para-carboxyphenyl)benzene compounds of the structural formula:

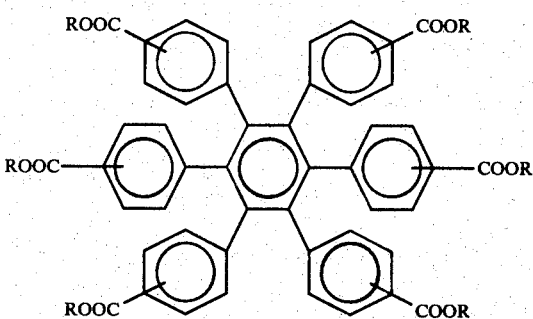

wherein R is selected from the group consisting of alkyl moieties of 1 to 24 carbon atoms and aryl moieties of 6 to 24 carbon atoms which comprises the cyclotrimerization of a compound selected from the group consisting of a 3,3'-dicarboalkoxytolan compound, a 4,4'-dicarboalkoxytolan compound, a 3,3'-dicarbophenoxytolan compound, a 4,4'-dicarbophenoxytolan compound, a 3,3'-dicarboaryloxytolan compound and a 4,4'-dicarboaryloxytolan compound wherein the alkoxy moiety can be of 1 to 24 carbon atoms and the aryl moiety can be from 6 to 24 carbon atoms in the presence of a suitable amount of dichlorobisbenzonitrilepalladium (II) as catalyst.

9. A compound which comprises the reaction product of a hexa-carboxyphenylbenzene compound of the structural formula

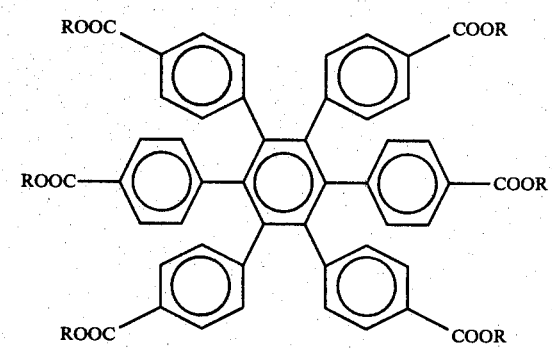

wherein the —OR moiety is halogen, and a reactant compound selected from the group consisting of 1,6-hexanediamine and 1,12-dodecanediamine, wherein the mole ratio of said hexa-carboxyphenylbenzene compound and said reactant compound is 1:3.

10. The compound of claim 9 wherein said hexa-carboxyphenylbenzene compound is an acyl chloride.

* * * * *